US00PP36781P2

(12) United States Plant Patent
Clark et al.

(10) Patent No.: US PP36,781 P2
(45) Date of Patent: Jul. 1, 2025

(54) BLACKBERRY PLANT NAMED 'A-2718T'

(50) Latin Name: ***Rubus* subgenus *Rubus* Watson**
Varietal Denomination: A-2718T

(71) Applicant: THE BOARD OF TRUSTEES OF THE UNIVERSITY OF ARKANSAS, Little Rock, AR (US)

(72) Inventors: John R. Clark, Fayetteville, AR (US); Margaret L. Worthington, Fayetteville, AR (US); Carmen A. Johns, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 18/831,157

(22) Filed: Aug. 20, 2024

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203, 204
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark |
| PP11,865 | P2 | 5/2001 | Clark |
| PP14,935 | P2 | 6/2004 | Clark |
| PP15,788 | P2 | 6/2005 | Clark |
| PP16,989 | P3 | 8/2006 | Clark |
| PP17,162 | P3 | 10/2006 | Clark |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz |
| PP26,405 | P3 | 2/2016 | Clark |
| PP26,413 | P3 | 2/2016 | Ortiz |
| PP26,990 | P3 | 8/2016 | Clark |
| PP27,032 | P2 | 8/2016 | Clark |
| PP27,401 | P3 | 11/2016 | Clark |
| PP28,598 | P3 | 11/2017 | Clark |
| PP33,115 | P2 | 5/2021 | Clark |
| PP33,330 | P2 | 7/2021 | Clark |
| PP34,867 | P2 | 12/2022 | Clark |
| PP35,368 | P2 | 9/2023 | Clark |
| PP35,552 | P2 | 12/2023 | Clark |

OTHER PUBLICATIONS https://www.thepacker.com/news/produce-crops/university-arkansas-releases-late-season-blackberry (retrieved from the Internet on Dec. 2, 2024).*
https://journals.ashs.org/hortsci/view/journals/hortsci/59/8/article-p1220.xml retrieved from the Internet on Dec. 2, 2024).*
Daugovish, O., et al. "Blackberry and Raspberry Cultivar Evaluations in Coastal California." HortTechnology 31.4 (2021): 552-558.
Ruple, A. et al., "An evaluation of fertility in Arkansas primocane-fruiting blackberries," (2010) Hort. Science 45:1-6.
Segantini, D.M., et al. "Physiochemical changes in floricane and primocane blackberries harvested from primocane genotypes." HortScience 53.1 (2018): 9-15.

* cited by examiner

*Primary Examiner* — Susan McCormick Ewoldt
(74) *Attorney, Agent, or Firm* — Quarles & Brady, LLP

(57) ABSTRACT

Description and specifications of a new and distinct blackberry cultivar named 'A-2718T' which originated from seed produced by a hand-pollinated cross 'A-2487T' (a non-patented, unreleased genotype) × 'A-2418T' (a non-patented, unreleased genotype). This new blackberry cultivar can be distinguished by its medium to large fruit size, firm berries, excellent crop, late season ripening, and good plant health.

3 Drawing Sheets

Latin name: *Rubus* subgenus *Rubus* Watson.
Varietal denomination: 'A-2718T'.

BACKGROUND

The new floricane-fruiting cultivar of blackberry called 'A-2718T' is described herein. The new cultivar originated from a hand-pollinated cross of Arkansas female selection 'A-2487T' (a non-patented, unreleased genotype) × Arkansas male selection 'A-2418T' (a non-patented, unreleased genotype) made in 2012. The seeds resulting from this controlled hybridization were germinated in a greenhouse in the spring of 2013 and planted in a field near Clarksville, Arkansas. (West-Central Arkansas). The seedlings fruited in the summer of 2015 and one seedling, designated 'A-2718T', was selected for its medium to large fruit weight, firm berries, excellent crop, late season ripening, and good plant health.

SUMMARY OF THE INVENTION

This new and distinct cultivar of blackberry originated from a hand-pollinated cross of Arkansas 'A-2487T' (a non-patented, unreleased genotype) × Arkansas 'A-2418T' (a non-patented, unreleased genotype) made in 2012 and located near Clarksville, Arkansas. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2013 and planted in a field near Clarksville, Arkansas. The seedlings fruited in the summer of 2015 on floricanes and one seedling, designated 'A-2718T', was selected for its medium to large fruit weight, firm berries, excellent crop, late season ripening, and good plant health.

During 2015, the original plant selection was propagated asexually from root cuttings at the above-noted location, and a test row of 10 plants was established. The proposed variety forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants from which the images were taken were 3 years old.

DETAILED DESCRIPTION OF THE NEW CULTIVAR 'A-2718T'

Figure 1:
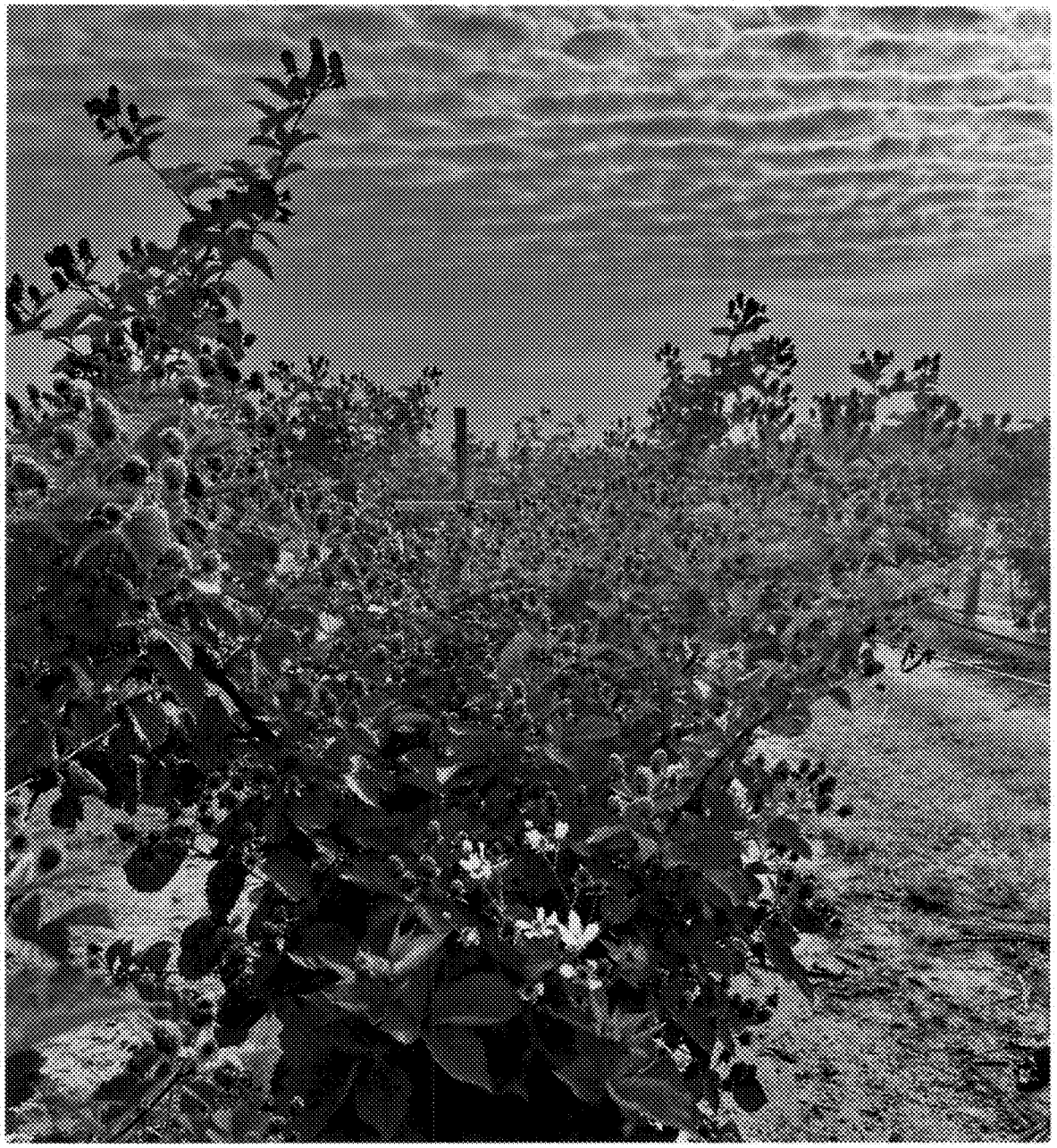
FIG. 1 is a photograph of a five-plant plot of 'A-2718T' with developing fruit on the plants.
Figure 2:
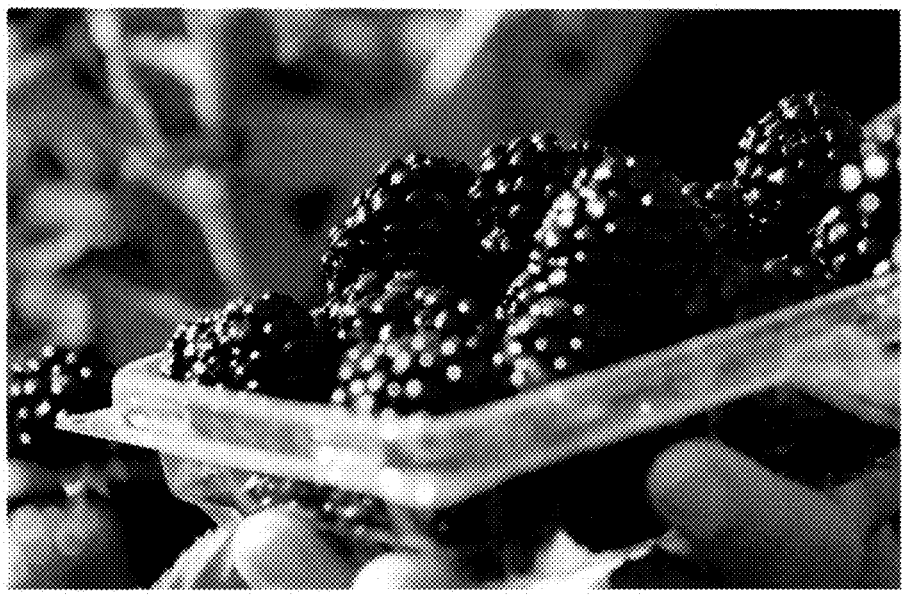
FIG. 2 is a photograph of ripe fruit of 'A-2718T'.
Figure 3:
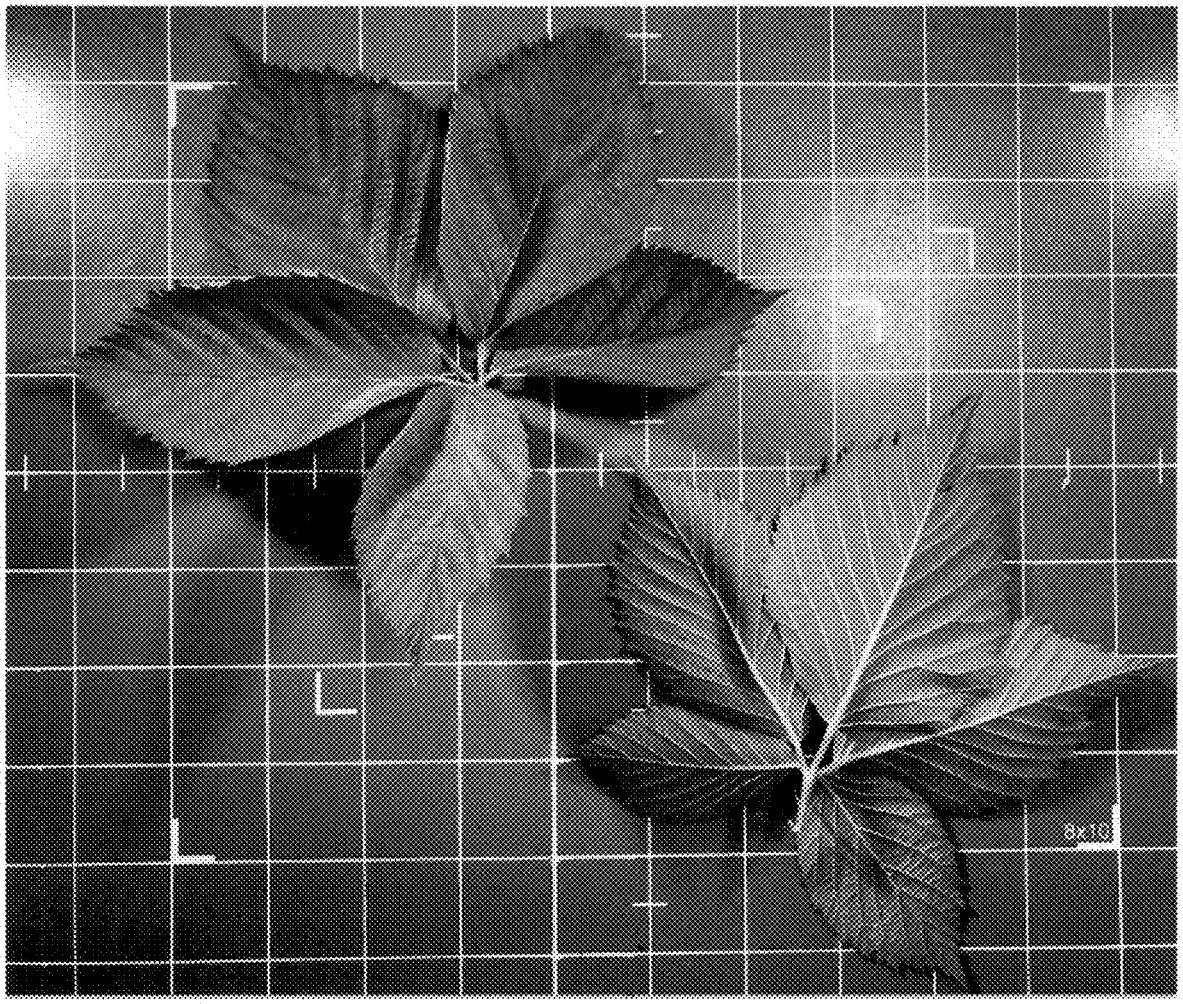
FIG. 3 is a photograph showing the abaxial (right) and adaxial (left) sides of a primocane leaf of 'A-2718T'.

Plants and fruit of this new cultivar differ phenotypically from its parents. The new cultivar has a larger fruit weight, ripens later, and crops more heavily than its female parent Arkansas 'A-2487T'. The new cultivar has similar fruit weight and is sweeter and less acidic on average than the male parent Arkansas 'A-2418T'. Fruit weight of 'A-2718T' is 7.4 grams, as compared to 4.12 grams for the female parent and 7.36 grams for the male parent. The Brix value for 'A-2718T' is 10.8, as compared to 12.0 and 9.1 for female and male parent, respectively. Although blackberries (*Rubus* subgenus *Rubus* Watson) are highly heterogeneous and outcrossing, and most clones contain genes from more than one species, the new cultivar and its progenitor lines predominantly exhibit phenotypic characteristics of the erect eastern United States species, *Rubus allegheniensis* (highbush blackberry).

Plants of the new cultivar are vigorous and prolific, and row establishment following planting is rapid. Both primocanes and floricanes are erect in growth habit. The canes perform best when a trellis with supporting wires is used to prevent canes from falling over due to wind or heavy fruit loads. The plants are thornless. Plants and fruit have shown slight susceptibility to anthracnose (*Elsinoe veneta*), and plants have shown no evidence of susceptibility to orange rust (*Gymnoconia nitens*). Plants have shown susceptibility to cane and leaf rust (*Kuehneola uredines*). No screening has been done for resistance to double blossom/rosette (*Cercosporella rubi*).

The bloom period of the new cultivar begins 26 April for 10% bloom, which is similar to 'Caddo' (U.S. Plant Pat. No. 33,115), also known as 'Sweet-Ark® Caddo', and 4 days later than 'Osage' (U.S. Plant Pat. No. 26,120). The average date for 90% bloom is 1 May, which is 2 days earlier than 'Caddo' and 3 days later than 'Osage'. Inflorescences are medium-large, cymose, and are mostly borne on the periphery of the plant canopy, providing easy access to harvest. Flower fertility is high, and clusters are well-filled.

Fruit of the new cultivar has an average first harvest date of 26 June and was approximately two weeks later than 'Caddo' and 'Osage'. The average floricane fruiting period is 40 days. Fruit yields of the new cultivar on floricanes averaged 4.4 kg/plant (9.7 lb/plant), similar to that of 'Osage' and 'Natchez' (U.S. Plant Pat. No. 20,891), and about 1.4 kg/plant less than that of 'Ponca' (U.S. Plant Pat. No. 33,330), also known as 'Sweet-Ark® Ponca', in West-Central Arkansas.

The fruit is elliptic to oblong in shape and glossy with a uniform black finish. The fruit is medium-large (ave. 7.4 g), larger than 'Osage' and 'Sweet-Ark® Ponca' and smaller than 'Sweet-Ark® Caddo' and 'Natchez'. Fruit weight of the new cultivar is maintained well throughout the entire harvest season. The new cultivar exhibits excellent fruit fertility with full drupelet set. Fruit of the new cultivar is very firm. Fruit firmness is a noteworthy characteristic of the new cultivar, as firmness contributes to shipping and storage potential. Storage potential of fresh fruit of the new cultivar exceeds that of 'Osage' and 'Sweet-Ark® Ponca' and is similar to that of 'Ouachita' (U.S. Plant Pat. No. 17,162) and 'Sweet-Ark® Caddo'. The flavor is balanced sweetness to tartness with occasional aromatic flavors. The soluble solids concentration averages 10.1% on shiny black fruit, which is lower than 'Osage', and 'Sweet-Ark® Caddo'. Titratable acidity averages 0.99 g/L (expressed as citric acid) and is higher than that of 'Osage' (0.67 g/L) and 'Sweet-Ark® Caddo' (0.83 g/L).

The dry seed weight for the new cultivar averaged 5.6 mg/seed, larger than 'Sweet-Ark® Ponca' and much smaller than 'Natchez' (10 mg/seed).

The following is a detailed description of the botanical and pomological characteristics of the subject blackberry. Color data are presented in Royal Horticultural Society Colour Chart designations (1986, 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with drip irrigation at or near Clarksville, Arkansas. The plants were fertilized near budbreak (late March on average) with complete or nitrogen fertilizer and had an additional nitrogen fertilizer application in early July. Primocanes were tipped at approximately 1.14 m (45 inches) and grown in a hedgerow training system including a trellis. Weeds were controlled with pre- and post-emergent herbicides supplemented with mechanical weed control activities. A single application of liquid lime sulfur was applied to the plants at budbreak, but no other fungicides were used. The descriptions reported herein are from specimens grown near Clarksville, Arkansas.

Plant:

*Size*.—Medium. Plants are grown in a hedgerow and primocanes tipped at approximately 1.14 m; plants in this system range in size from approx. 107-140 cm tall and 91-102 cm wide.

*Growth habit*.—Upright, moderate vigor, canes erect; suckers from the crown and roots.

*Growth rate*.—First primocane emergence date: 7 April. Primocanes reach tipping height: 19 May. Floricane first budbreak: 10 March. 10% bloom: 26 April. First ripe fruit: 26 June.

Productivity:

*Floricane*.—4.4 kg (9.7 lb/plant) when no winter injury was experienced.

*Cold hardiness*.—Hardy to −10° F. (−23.3° C.). The new cultivar has not been exposed to lower temperatures, but would likely experience bud and cane injury at lower temperatures.

Canes: Thornless, erect.

Floricane (dormant or winter cane):

*Cane diameter*.—Base: 1.53 cm; midpoint: 1.11 cm; terminus: 1.02 cm.

*Internode length*.—Base: 6.45 cm; midpoint: 4.73 cm; terminus: 3.95 cm.

*Floricane color*.—Base: yellow-green group (146B); midpoint: yellow-green group (146B); terminus: yellow-green group (146B); sun-exposed areas of floricanes have anthocyanins present: red-purple group (60A).

Primocane (current-season cane; late summer):

*Cane diameter*.—Base: 1.45 cm; midpoint: 1.02 cm; terminus: 0.79 cm.

*Internode length*.—Base: 8.68 cm; midpoint: 5.32 cm; terminus: 3.81 cm.

*Primocane color*.—Base: yellow-green group (146A); midpoint: yellow-green group (146A); terminus: yellow-green group (146B); sun-exposed areas of floricanes have anthocyanins present: greyed-purple group (187A).

*Thorn density* (*per* 30 *cm of cane length*).—Not applicable, this plant is thornless.

*Disease resistance*.—Plants and fruit have shown moderate tolerance to anthracnose, and plants have shown no evidence of susceptibility to orange rust. Plants have shown moderate tolerance to cane and leaf rust. No screening has been done for resistance to double blossom/rosette, but thornless material from this program has shown to be tolerant in the past.

*Lateral branching after tipping* (*measured at the end of growing season*).—Average number of lateral branches: 3-5; distribution concentrated on the distal portion (top one-third) of the canes.

Foliage:

Primocane:

*Leaves*.—Medium; mature compound leaf width: 11.8 cm; length: 9.9 cm; overall shape: palmate, multifoliate (5).

*Glossiness*.—Abaxial: dull, not glossy; adaxial: slightly glossy.

*Color*.—Base: abaxial: green group (138B); adaxial: green group (137A); midpoint: abaxial: green group (138B); adaxial: green group (137A); terminus: abaxial: green group (138B); adaxial: green group (137A).

*Leaflet*.—Width: 7.4 cm; length: 9.9 cm; shape: ovate with an acuminate apex and rounded base; margin is biserrate; serration teeth length is 0.32 cm and width is 0.29 cm; number of leaflets per compound leaf: 5; venation: pinnate; young leaf abaxial: vein color: yellow-green group (145B); young leaf: adaxial vein color: yellow-green group (145A); mature leaf: abaxial leaf vein color: yellow-green group (145B); mature leaf: adaxial vein color: yellow-green group (145A); no lobing on leaflets, moderate undulation present.

*Petioles*.—Length: 2.85 cm; diameter; 0.29 cm; color: abaxial: yellow-green group (144B); adaxial: yellow-green group (144B); texture is moderate pubescence.

*Petiolules*.—Length: 1.11 cm; diameter: 0.19 cm; color: abaxial: yellow-green group (144C) and adaxial: yellow-green group (144C); texture is moderate to heavy pubescence.

*Stipules*.—2 per leaf; length: 1.15 cm; width: 0.18 cm; texture: moderate pubescence is present on both the abaxial and adaxial surfaces; shape: overall shape is subulate; apex shape: acuminate; base shape: truncate; margins are smooth; color: abaxial: yellow-green group (144C), adaxial: yellow-green group (144C).

Floricane:

*Leaves*.—Medium; mature compound leaf width: 11.8 cm; length: 9.9 cm; overall shape: compound palmate, trifoliate.

*Average date of leaf bud burst*.—10 March.

*Glossiness*.—Abaxial: dull, heavy pubescence; adaxial: slightly glossy, light pubescence present.

*Color*.—Base: abaxial: yellow-green group (147B); adaxial: yellow-green group (147A); midpoint: abaxial: yellow-green group (147B); adaxial: yellow-green group (147A); terminus: abaxial: yellow-green group (147B); adaxial: yellow-green group (147A).

*Leaflet*.—Width: 5.2 cm; length: 7.9 cm; shape: ovate with acute apex and acute at the base; margin is biserrate; serration teeth length is 0.21 cm and width 0.19 cm; number of leaflets per compound leaf: 3; venation pinnate; young leaf: abaxial vein color: yellow-green group (147B); adaxial vein color: green group (137A); mature leaf: abaxial leaf vein color: yellow-green group (152D); adaxial vein color: yellow-green group (152D); no lobing on leaflets, undulation is absent on floricane leaflets.

*Petioles*.—Length: 1.48 cm; color: abaxial side is yellow-green group (146D); adaxial surface yellow-green group (146D); diameter: 0.20 cm; texture is heavy pubescence present.

*Petiolules*.—Length: 0.82 cm; diameter: 0.13 cm; color: abaxial surface is yellow-green group (146D); adaxial surface is yellow-green group (146D); texture is heavy pubescence.

*Stipules*.—2 per leaf; length: 0.76 cm; width: 0.16 cm; texture: light pubescence is present on both the abaxial and adaxial surfaces of primocane stipules; shape: overall: subulate; apex: acuminate; base: truncate; margins are smooth; color: abaxial surface: yellow-green group (147B), adaxial surface: green group (137A).

Flowers:

Floricane:

*Date of bloom*.—First bloom: 26 April; 90% bloom: 1 May.

*Reproductive organs*.—Stamens: erect, numerous. Pistils: numerous. Pollen: normal, fertile, and abundant.

*Flower*.—Diameter: 4.65 cm; depth: 1.72 cm; shape: overall rotate; symmetry: actinomorphic.

*Petals*.—Number per flower: 6; length: 2.17 cm; width: 1.36 cm; shape overall: oblanceolate; apex: rounded; margin: smooth, undulate; base: cuneate to acute; color: abaxial surface: white group (155C) with red-purple group (69B); adaxial surface: white group (155C) with red-purple group (69B); texture: abaxial: smooth, no pubescence; adaxial: smooth, no pubescence.

*Flowers per cluster.*—9.

*Sepal.*—Number per flower: 5; length: 1.19 cm; width: 0.54 cm; shape: overall: lanceolate; apex: acuminate; margin: entire (smooth); base: truncate; texture: abaxial: moderate to heavy pubescence; adaxial: light pubescence; color: abaxial: yellow-green group (146B); adaxial: yellow-green group (146C).

*Pedicel.*—Length: 2.44 cm; width: 0.13 cm; color: yellow-green group (146C); texture: heavy pubescence.

*Peduncle.*—Length: 1.10 cm; width: 0.42 cm; color: yellow-green group (145B).

*Cyme.*—Type: elongated simple cyme; length: 22.80 cm.

Fruit:

*Maturity.*—Average first ripe date: 26 June; Average fruiting period: 40-50 days.

*Weight.*—Medium, ave. 7.4 g.

*Diameter of fruit at primary position on inflorescence.*—Equator: 2.36 cm; base pole: 2.31 cm; terminal pole: 1.67 cm.

*Diameter of fruit at secondary positions on inflorescence.*—Equator: 2.13 cm; base pole: 1.91 cm; terminal pole: 1.56 cm.

*Primary fruit.*—Length: 3.18 cm; shape: elliptic to oblong; color: black group (202A).

*Drupelet size.*—0.59 cm.

*Drupelet number per fruit.*—68.

*Seed.—Average length:* 0.36 cm; width: 0.25 cm; dry weight: 5.60 mg; wet weight: 8.10 mg; color: wet orange group (24C); color: dry greyed-orange group (165C).

*Soluble solids.*—10.1%.

*pH.*—3.30.

*Titratable acidity.*—0.99 g/L expressed as citric acid.

*Processed quality.*—Not evaluated for processing.

*Uses.*—Commercial cultivar with excellent potential for shipping, as well as an option for local-market production and home gardens.

The cultivar: The most distinctive features of the cultivar are medium to large fruit weight, firm berries, excellent crop, late-season ripening, and good plant health.

We claim:

1. A new and distinct cultivar of blackberry plant named 'A-2718T', substantially as illustrated and described herein.

* * * * *